US006534505B2

(12) United States Patent
Kaufman et al.

(10) Patent No.: US 6,534,505 B2
(45) Date of Patent: Mar. 18, 2003

(54) THERAPEUTIC POLYMORPHS OF A GABA-A ALPHA-5 INVERSE AGONIST AND PAMOATE FORMULATIONS OF THE SAME

(75) Inventors: Michael J. Kaufman, New Hope, PA (US); Daniel J. Rush, Philadelphia, PA (US)

(73) Assignee: Merck & Co., Inc., Rahway, NJ (US)

( * ) Notice: Subject to any disclaimer, the term of this patent is extended or adjusted under 35 U.S.C. 154(b) by 37 days.

(21) Appl. No.: 09/728,497

(22) Filed: Nov. 30, 2000

(65) Prior Publication Data

US 2001/0049439 A1 Dec. 6, 2001

Related U.S. Application Data

(62) Division of application No. 09/437,928, filed on Nov. 10, 1999.
(60) Provisional application No. 60/108,007, filed on Nov. 12, 1998.

(51) Int. Cl.$^7$ .................. C07D 487/04; A01K 31/5025; A61P 25/28
(52) U.S. Cl. ....................... 514/248; 544/234
(58) Field of Search ............................ 514/248; 544/234

(56) References Cited

U.S. PATENT DOCUMENTS 4,007,167 A  *  2/1977  Martin et al. .................. 536/17
4,237,120 A  *  12/1980  Ingle ........................... 424/181
4,291,026 A  *  9/1981  Tobkes et al. .............. 424/181

FOREIGN PATENT DOCUMENTS

| EP | 0 085 840 | 8/1983 |
| EP | 0 134 946 | 3/1985 |
| GB | 1059508 | 2/1967 |
| WO | WO 96/25948 | 8/1996 |
| WO | WO 98/50385 | 11/1998 |

OTHER PUBLICATIONS

D. Cai, et al., Tetrahedron Lett., 37: 2537–2540 (1996).
W. Holzer and K. Ruso, J. Heterocyclic Chem., 29: 1203–1207 (1992).
R.G.M. Morris, Learning and Motivation, 12: 239–260 (1981).

* cited by examiner

*Primary Examiner*—Mukund J. Shah
*Assistant Examiner*—Thomas C McKenzie
(74) *Attorney, Agent, or Firm*—J. Eric Thies; Shu M. Lee; Melvin Winokur (57) ABSTRACT

There is disclosed 3-(5-methylisoxazol-3-yl)-6-(1-methyl-1,2,3-triazol-4-yl)methyloxy-1,2,4-triazolo[3,4-a]phthalazine in the form of a dihydrate, a dehydrate of the dihydrate and a pentahydrate, pharmaceutical compositions comprising the forms, the use of the forms for enhancing cognition, processes for producing the forms, their incorporation in pharmaceutical compositions comprising pamoate ions and the use of such ions for solubilizing neutral molecules.

8 Claims, 7 Drawing Sheets

THERAPEUTIC POLYMORPHS OF A GABA-A ALPHA-5 INVERSE AGONIST AND PAMOATE FORMULATIONS OF THE SAME

This is a divisional of U.S. application Ser. No. 09/437,928 filed Nov. 10, 1999, and claims the benefit of U.S. Provisional Application Ser. No. 60/108,007 filed Nov. 12, 1998.

The present invention relates to polymorphs of a substituted triazolo-phthalazine derivative, to their use in therapy, to compositions containing them and to processes for their manufacture. The present invention also relates to a pamoate formulation of the derivative and to new uses of pamoate ions.

BACKGROUND OF THE INVENTION

We have now discovered that it is possible to obtain medicaments which have cognition enhancing effects which may be employed with less risk of proconvulsant effects previously described with benzodiazepine receptor partial or full inverse agonists. Inverse agonists which are inverse agonists for the α5 receptor and are relatively free of activity at α1, α2 and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

BRIEF SUMMARY OF THE INVENTION

The present invention provides 3-(5-methylisoxazol-3-yl)-6-(1-methyl-1,2,3-triazol-4-yl)methyloxy-1,2,4-triazolo[3,4-a]phthalazine in the form of a dihydrate.

There is also provided 3-(5-methylisoxazol-3-yl)-6-(1-methyl-1,2,3-triazol-4-yl)methyloxy-1,2,4-triazolo[3,4-a]phthalazine in the dehydrated form of the dihydrate.

There is further provided 3-(5-methylisoxazol-3-yl)-6-(1-methyl-1,2,3-triazol-4-yl)methyloxy-1,2,4-triazolo[3,4-a]phthalazine in the form of a pentahydrate.

These polymorphs are new and may be advantageous, for example, for ease of processing, handling or dosing of the compound. They may, in particular, have improved chemical properties such as solubility, stability or rate of solution. In particular, they may be particularly suitable for manufacture of dosage forms. Examples of dosage forms are mentioned later.

International Patent Application No. PCT/GB98/01307 discloses 3-(5-methylisoxazol-3-yl)-6-(1-methyl-1,2,3-triazol-4-yl)methyloxy-1,2,4-triazolo[3, 4-a]phthalazine which compound is useful for enhancing cognition. There is no specific disclosure or discussion of the crystal forms of this compound.

The dihydrate may be prepared by mixing a saturating amount of 3-(5-methylisoxazol-3-yl)-6-(1-methyl-1,2,3-triazol-4-yl)methyloxy-1,2,4-triazolo [3,4-a]phthalazine with 5% aqueous di-sodium pamoate for several days. The dihydrate can be isolated by filtering the product.

The dihydrate may alternatively be produced by mixing a saturating amount of 3-(5-methylisoxazol-3-yl)-6-(1-methyl-1,2,3-triazol-4-yl)methyloxy-1,2,4-triazolo[3,4-a]phthalazine with USP water. The solids obtained from filtering the product are partially in dihydrate form.

A further method of producing the dihydrate is to mill (i.e. nanonise) the anhydrous form of 3-(5-methylisoxazol-3-yl)-6-(1-methyl-1,2,3-triazol-4-yl)methyloxy-1,2,4-triazolo[3, 4-a]phthalazine in accordance with details disclosed in U.S. Pat. No. 5,145,684.

Another method for producing the dihydrate is to dissolve the anhydrous form in glacial acetic acid and water in about a 39:9 mixture, followed by hot filtration, the addition of a large amount of water of about four times the volume of the mixture, and ageing at room temperature for from 2 to 40 hours before filtration of the final product.

The dehydrate may be prepared by gentle heating of the dihydrate or pentahydrate in a vacuum oven from 30° C. to 100° C. for about 20.5 hours generally under dry nitrogen purge.

The pentahydrate may be produced by adding excess solid 3-(5-methylisoxazol-3-yl)-6-(1-methyl-1,2,3-triazol-4-yl)methyloxy-1,2,4-triazolo[3,4-a]phthalazine to water or organic solvents with sufficient water present and generally stirring for several hours, such as about 12 hours, generally at room temperature. The pentahydrate can be isolated by filtering the product. Examples of water/organic solvents are ethyl acetate (saturated with water), acetonitrile (1/1 with water), acetic acid (20/80 with water), acetone (20/80 with water) and tetrahydrofuran (1/1 with water). The pentahydrate is preferably stored at humidities above 93%.

DETAILED DESCRIPTION OF THE INVENTION

X-ray powder diffraction studies are widely used to elucidate molecular structures, crystallinity and polymorphism. X-ray powder diffraction (XRPD) patterns were collected using a Siemens Diffraktometer with a Kristalloflex copper Kα radiation. Measurements were made from 4° to 40° (2 theta) with the sample maintained at ambient room temperature.

Figure 1:
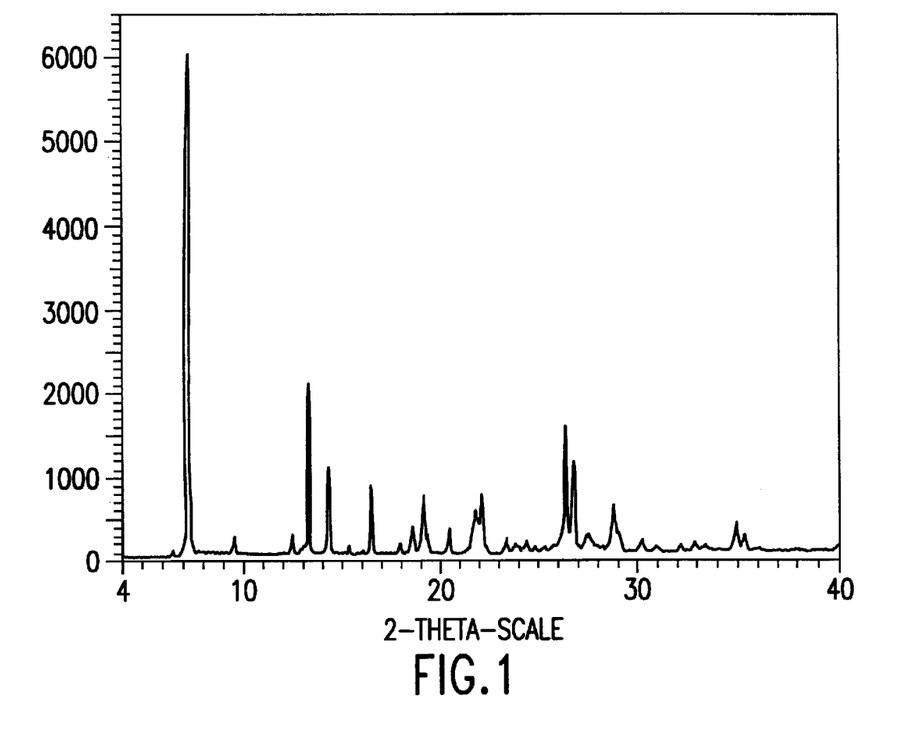
FIG. 1 shows the X-ray diffraction pattern from the dihydrate.
Figure 9:
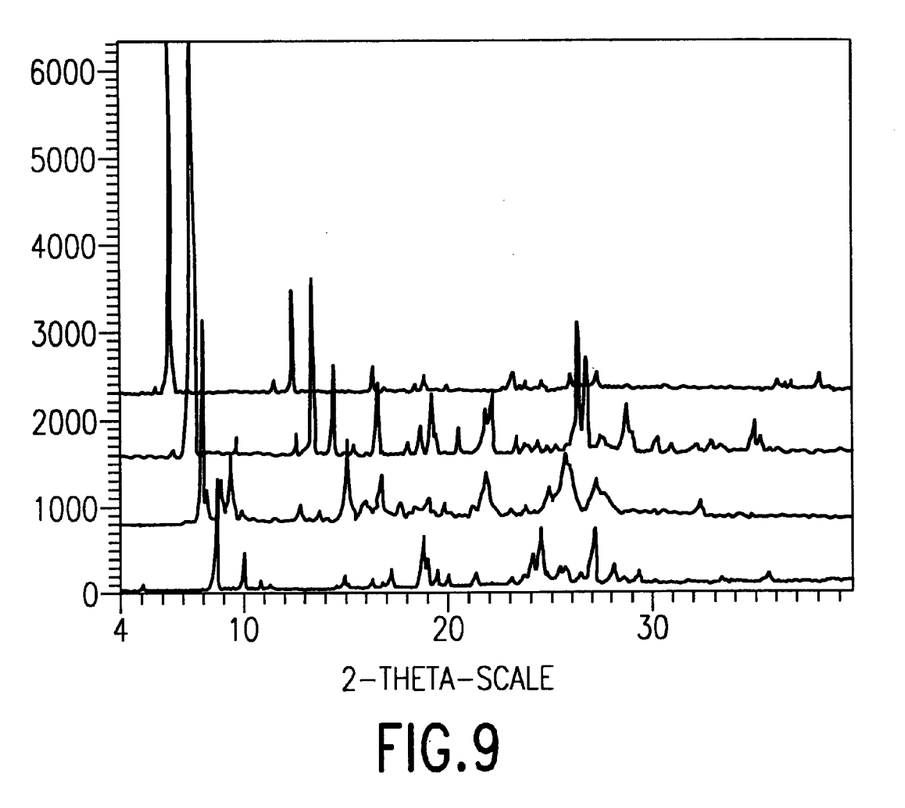
FIG. 9 shows from top to bottom, the patterns being offset vertically for visual clarity, the X-ray diffraction patterns for the pentahydrate compound (top), the dihydrate, the dehydrate, and the anhydrous (bottom).

The dihydrate was characterised by an X-ray powder diffraction pattern with a principal reflection at 7.2 deg (2 theta). In particular the reflections in order of intensity with an accuracy of ±0.2 degrees are 7.2, 13.3, 26.3, 26.7, 14.4, 16.5, 19.2 and 22.1 degrees.

Figure 5:
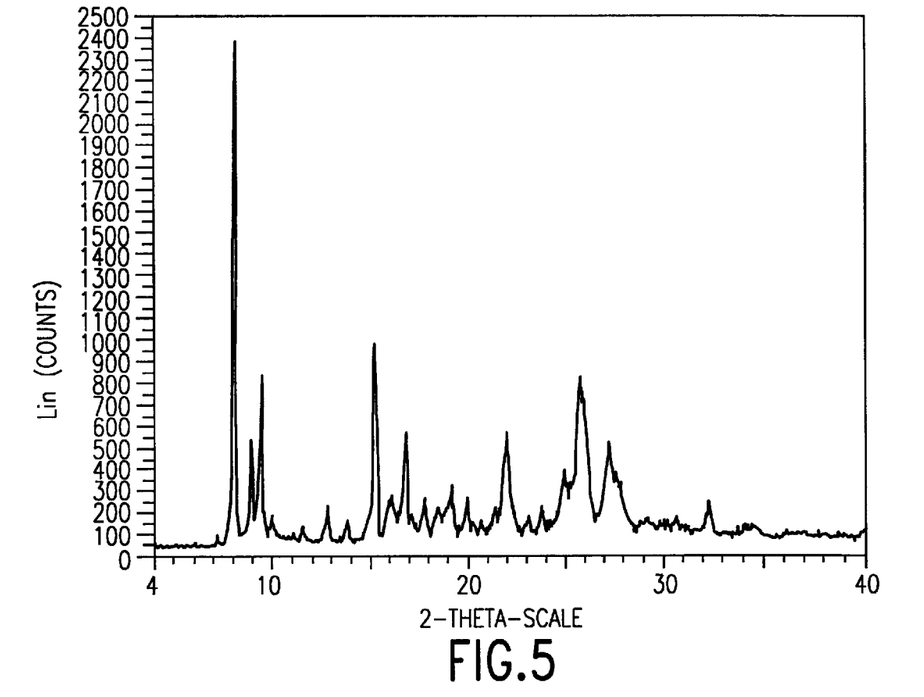
FIG. 5 shows the X-ray diffraction pattern for the dehydrate.

The dehydrate was characterised by an X-ray powder diffraction pattern with a principal reflection at approximately 7.9 deg (2 theta). Its pattern gives reflections at the following d-spacings in order of intensity and with an accuracy of ±0.2 degrees: 7.9, 15.1, 9.3, 25.7, 8.8, 16.7, 21.9 and 27.2 degrees.

Figure 10:
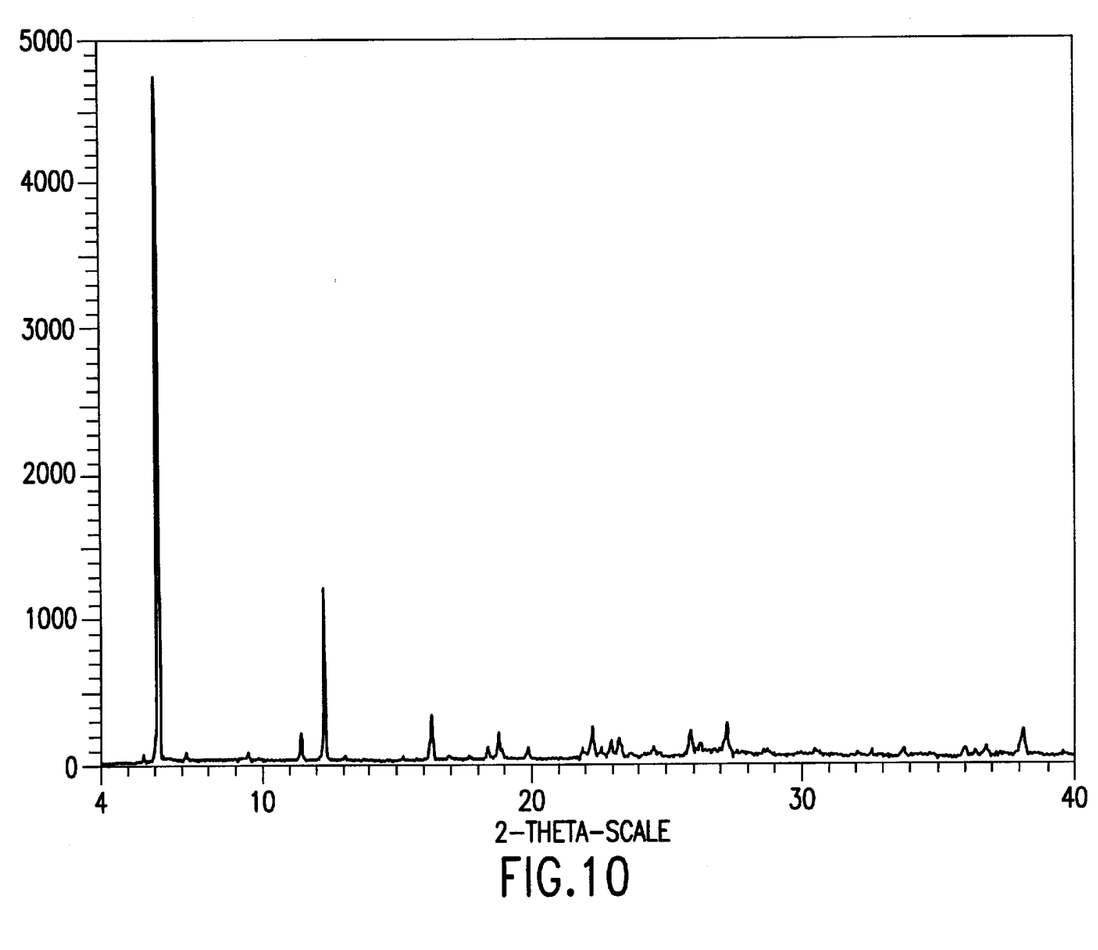
FIG. 10 shows the X-ray diffraction pattern for the pentahydrate.

The X-ray powder diffraction pattern of the pentahydrate shows a principal reflection at 6.1 deg (2 theta). The reflections in order of intensity and with an accuracy of ±0.2 degrees are 6.1, 12.3, 16.3, 11.4, 18.8, 22.3, 27.3 and 38.1 degrees.

Figure 2:
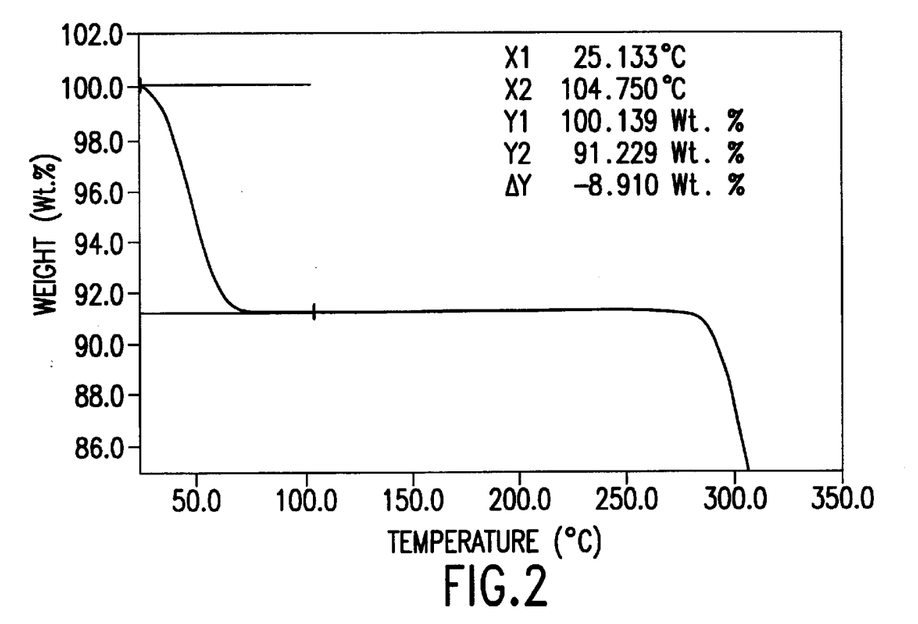
FIG. 2 shows the thermal gravimetric analysis data for the dihydrate.

The Thermal Gravimetric Analysis (TGA) data for the dihydrate shows a loss of 8.910% mass upon heating in a nitrogen corresponding to the correct mass loss for 1.97 moles of water.

Figure 6:
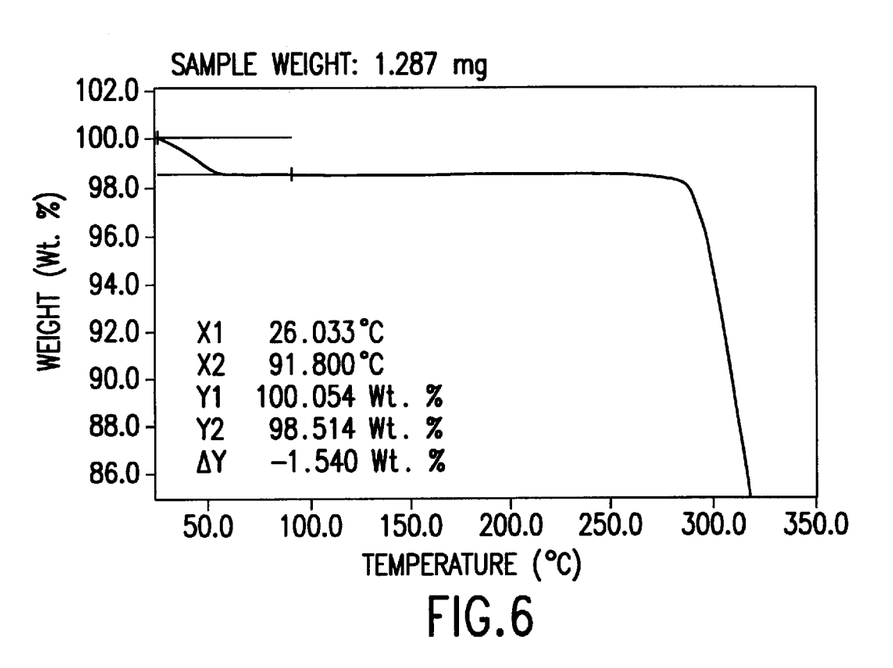
FIG. 6 shows the thermal gravimetric analysis for the dehydrate.

The TGA data for the dehydrate shows a loss of 1.5% mass upon heating in a nitrogen stream corresponding to the loss of 0.33 moles of water. This is considered to be caused by the dehydrate having undergone insufficient heating to drive all water out of the crystal matrix; in addition, or in the alternative, the dehydrate may be hygroscopic.

Figure 3:
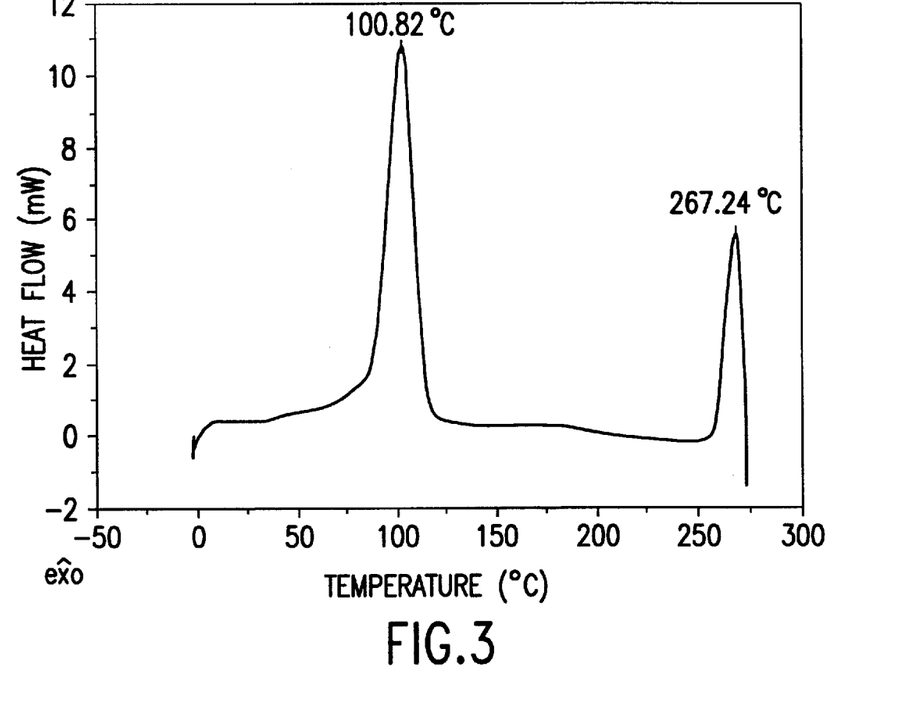
FIG. 3 shows the differential scanning calorimetry curve for the dihydrate.

Differential Scanning Calorimetry (DSC) of the dihydrate did not differ significantly in its high temperature endotherm peak from the anhydrous form (267.2° C. and 267.5° C. respectively). The second large endotherm did differ significantly being at 100.8° C. whereas the anhydrous form has no other endotherm. This is consistent with being a dihydrate.

Figure 7:
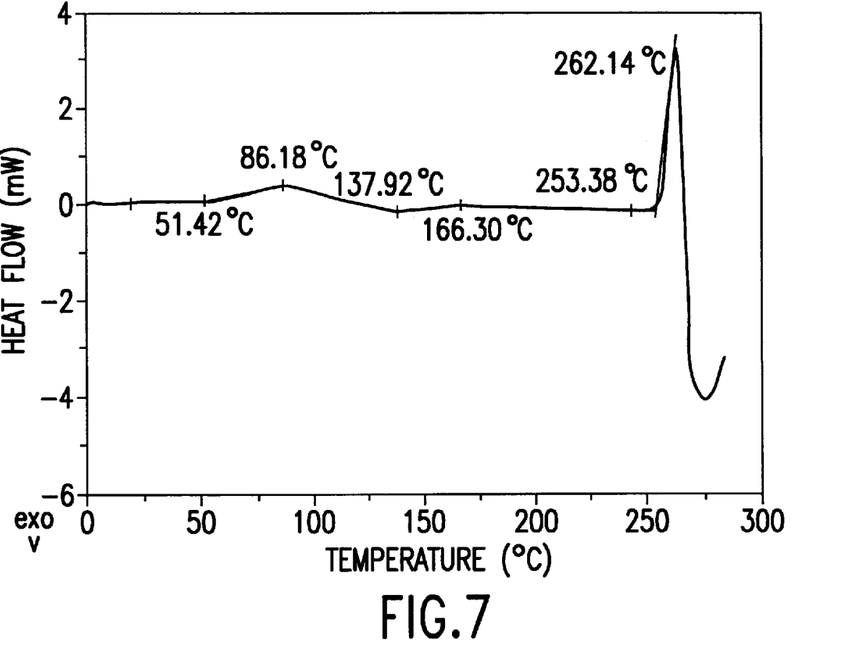
FIG. 7 shows the differential scanning calorimetry curve for the dehydrate.

DSC data for the dehydrate show a high temperature endotherm of 262.1° C. indistinguishable from that of the anhydrous control at 262.6° C. This series of DSC was run at a slower scan rate thus explaining the apparent difference in peak maxima. A small endotherm for the dehydrate is present at 86° C. consistent with the residual presence of a small amount of water. A small exotherm was seen at 138° C.

Figure 11:
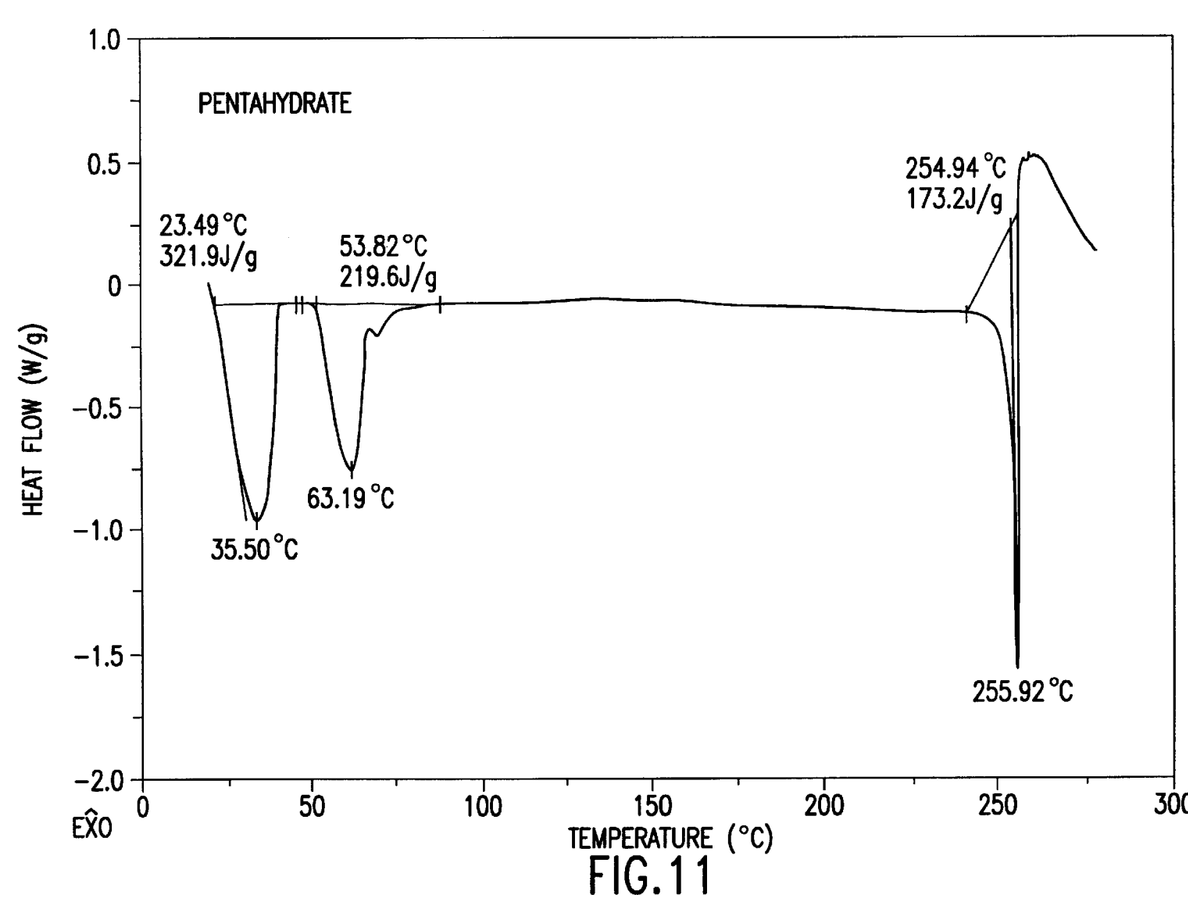
FIG. 11 shows the differential scanning calorimetry curve for the pentahydrate.

DSC data for the pentahydrate show a high temperature melting-decomposition endotherm with a peak at 256° C., and two water loss endotherms with peaks at 36 and 63° C. (at 2° C./min under $N_2$ saturated with water vapour at 21.3° C.).

A 1.155 mg sample of the dihydrate was carefully weighed and dissolved to 25.0 ml volume with 50150 MeCN/$H_2O$. The resulting solution was analysed by HPLC against standard concentration curves made from the anhydrous form. Quantitation indicated a peak area of 90.6% of theoretical which is within the experimental error of the value expected for a dihydrate at 91.0% of theoretical.

Figure 4:
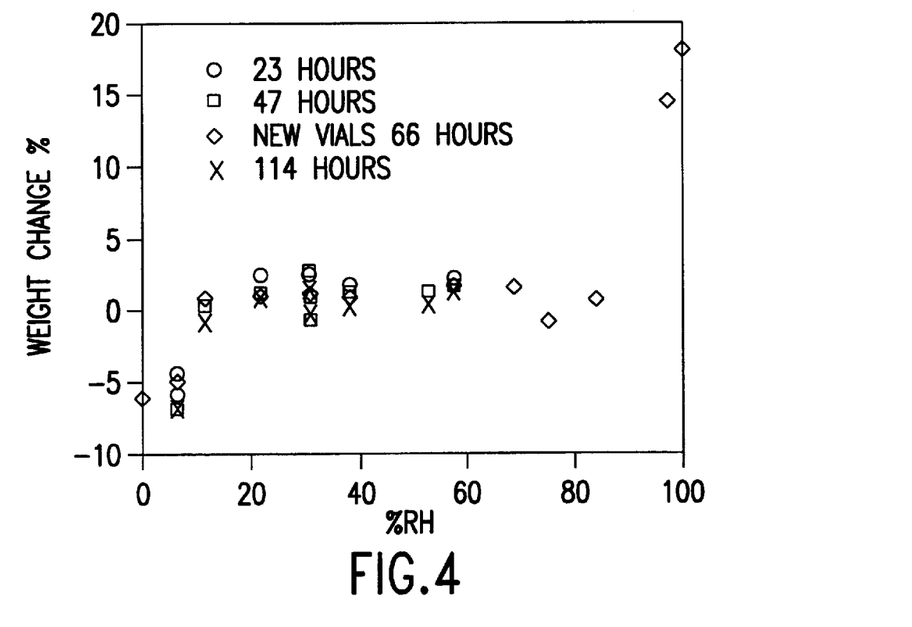
FIG. 4 shows the gravimetric determination of dihydrate hygroscopicity.

The hygroscopicity of the dihydrate was determined gravimetrically in a series of constant humidity jars equilibrated over 1-5 days. The data indicated a significant window of stability between 20 and 80% relative humidity at 25° C. At low humidity the loss of water was reasonably close to that determined by TGA. At high humidity the material gained mass (water) by an amount corresponding to between 2 and 5 moles of water per mole.

It appears that the dihydrate is the low energy species. It is not synthesised directly from the anhydrate but via the pentahydrate, drying of which yields the dihydrate.

The present invention also provides a pharmaceutical composition comprising 3-(5-methylisoxazol-3-yl)-6-(1-methyl-1,2,3-triazol-4-yl)methyloxy-1,2,4-triazolo[3,4-a]phthalazine and pamoate ions.

The pamoate ions are generally derived from dissolving disodium pamoate in a solvent such as water, however the pamoate ions may be provided in combination with any suitable cation such as in the form of the calcium, lithium or potassium salts.

The use of pamoate ions to solubilize a neutral molecule is new. Thus the present invention also provides a composition comprising pamoate ions and an active compound which is a neutral molecule. In particular, the composition is a pharmaceutical or veterinary composition.

The present invention further provides the use of pamoate ions for solubilizing neutral molecules which are preferably pharmaceutically or veterinarily active. The stabilisation of molecules outside the field of human or animal health is also provided.

Pamoate ions, either in the form of disodium pamoate or in the form of the acid, are commercially available. Compounds comprising pamoate ions and various cations can be made by the skilled man by methods well known in the art.

The amount of disodium pamoate (or its equivalent in pamoate ions) preferably included in compositions comprising 3-(5-methylisoxazol-3-yl)-6-(1-methyl-1,2,3-triazol-4-yl)methyloxy-1,2,4-triazolo [3,4-a]phthalazine is from 0.01% to 20% w/v, in particular from 1% to 15% w/v and especially from 3% to 13% w/v. It is contemplated that similar amounts would generally be used with other active ingredients.

Pamoate formulations of 3-(5-methylisoxazol-3-yl)-6-(1-methyl-1,2,3-triazol-4-yl)methyloxy-1,2,4-triazolo[3,4-a]phthalazine provide excellent solubility of the active compound thus having utility for increasing its oral bioavailability in any suitable dosage form such as tablets, capsules and suspensions. Further examples of standard dosage forms are detailed below. It is contemplated that similar benefits would be seen with other neutral molecules. Improved solubility is, of course, important in a wide range of applications where provision of an active compound which is a neutral molecule to a location is desired.

There is also provided solid formulations comprising pamoate anions, a cation and a neutral molecule. In particular the solid formulations are for use with veterinary or pharmaceutical neutral molecules in which case the cation is veterinally or pharmaceutically acceptable. Pharmaceutical solid formulations are particularly contemplated.

Such solid formulations surprisingly enhance solubilization of the neutral molecule upon administration to a liquid environment.

It is contemplated that any of the crystal forms may be given as a pamoate formulation depending on the precise conditions used; these conditions could readily be identified by the skilled man. In particular, dosing in pamoate formulation is preferred for the dihydrate.

In a particularly favoured embodiment these is provided an enterically coated solid pharmacuetical or veterinary formulation of a neutral pharmaceutical or veterinary compound, pamoate ions and a pharmaceutically or veterinally acceptable cation. It has suprisingly been found that pamoate ions better stabilize neutral molecules at high pH. Thus an enterically coated solid formulation prevents exposure of the pamoate formulation to the high acidity of the stomach which might otherwise tend to precipitate the neutral molecule and instead allows exposure of the pamoate formulation with the neutral compound to the relatively higher pH of the gut thus surprisingly enhancing bioavilability of the neutral compound. The neutral compound is preferably a pharmaceutical compound, particularly 3-(5- methylisoxazol-3-yl)-6-(1-methyl-1,2,3-triazol-4-yl) methyloxy-1,2,4-triazolo[3,4-a]phthalazine. Particularly favoured enteric coatings include Surerelease™, Aquacoat® CPD and Sureteric®. Surerelease™ is particularly favoured. The coatings are applied in a conventional manner well known to the person skilled in the art.

Thus, for example, the polymorphs of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

The invention also provides pharmaceutical compositions comprising a polymorph of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a polymorph of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides the use of a polymorph of the present invention in the manufacture of a medicament for the enhancement of cognition, preferably in a human suffering from a dementing illness such as Alzheimer's disease.

For the enhancement of cognition, a suitable dosage level is about 0.01 to 250 mg/kg per day, preferably about 0.01 to 100 mg/kg per day, and especially about 0.01 to 5 mg/kg of body weight per day. The polymorph may be administered on a regimen of 1 to 4 times per day. In some cases, however, dosage outside these limits may be used.

It is preferred that the polymorphs of the present invention be ground, for example using a pestle and mortar or industrial equivalent thereto, to a particle size of between 1 and 10 $\mu$M, and preferably less than 5 $\mu$M, before formulation. The polymorphs may be micronised or sonicised by methods known in the art. The dihydrate may be nanonised, for example by methods disclosed in U.S. Pat. No. 5,145,684, and the dehydrate be formed therefrom as described above.

The polymorphs in accordance with this invention potently inhibit the binding of [$^3$H]-flumazenil to the benzodiazepine binding site of human $GABA_A$, receptors containing the $\alpha 5$ subunit stably expressed in Ltk cells.

The compound of the accompanying Reference (i.e. the anhydrous form) Examples was tested in the above assay, and was found to possess a Ki value for displacement of [$^3$H]Ro 15-1788 from the $\alpha 5$ subunit of the human $GABA_A$ receptor of 100 nM or less.

The compound of the accompanying Reference Examples (i.e. the anhydrous form) has been shown to enhance cognition in the rat water maze test (Morris, Learning and Motivation, 1981, 12, 239ff. Further details of methodology for demonstrating that the present compounds enhance cognition can be found in WO-A-9625948. This has been demonstrated at a minimum effective dose of 0.3mg/kg at which the compound of the present invention has 40% receptor occupancy. It has also been demonstrated at a dose of 3 mg/kg.

The anhydrous form of the compound used in the present invention can be made as described in following Reference Examples. Precise details of the reaction conditions, and obvious modifications of the reaction procedure, are well within the capabilities of the skilled person.

Intermediate 1

6-Chloro-3-(5-Methylisoxazol-3-yl)-1,2,4-triazolo [3,4-a] phthalazine a) 1-Chloro-4-hydrazinophthalazine 1,4-Dichlorophthalazine (20.0g, 0.100 mol) was added to a boiling solution of hydrazine monohydrate (37.3 ml, 0.765 mol) in ethanol (500 ml) and the mixture heated at reflux for 0.5 h. The mixture was cooled to room temperature and the solid collected by filtration and washed with ether. The material was taken with n-butanol and ammonia solution (sp. gr. 0.91) and heated until the solid dissolved. The organic layer was separated, evaporated in vacuo and the residue azeotroped with xylene (x2) and dried in vacuo to give the title-hydrazine (11.5 g, 59%), $^1$H NMR (250 MHz, d$^6$DMSO) δ 7.84-8.04 (3H, m, Ar—H), 8.20 (1H, m, Ar—H); MS (ES$^+$) m/e 194 [MH]$^+$.

b) 5-Methylisoxazole-3-carboxylic acid

A mixture of acetonylacetone (10 g, 88 mmol) and nitric acid (sp. gr. 1.42)/water (2:3) (50 ml) was cautiously brought to reflux under a stream of nitrogen and boiled for 1 h. The solution was cooled to room temperature and aged overnight. The resultant solid was collected by filtration, washed with chilled water (2×7 ml) and hexane, and dried in vacuo to give the title-acid (4.4 g, 40%), $^1$H NMR (CDCl$_3$) δ 2.50 (3H, d, J=0.8 Hz, Me), 6.41 (1H, d, J=0.8 Hz, Ar—H).

c) 6-Chloro-3-(5-Methylisoxazol-3-yl)-1,2, 4-triazolo[3,4-a]phthalazine

5-Methylisoxazole-3-carboxylic acid (5.24 g, 41.3 mmol), bis(2-oxo-3-oxazolidinyl)phosphinic chloride (10.5 g, 41.2 mmol) and triethylamine (11.5 ml, 82.5 mmol) were added successively to a stirred suspension of 1-chloro-4-hydrazinophthalazine (8.00 g, 41.2 mmol) in dichloromethane (11) at 0° C. under nitrogen. The mixture was stirred at 0° C. for 2 h and at room temperature overnight. The solvent was evaporated in vacuo, the residue triturated with water and the solid filtered off, washed with hexane and dried in vacuo to give the ketohydrazine (11 g), MS (ES$^+$) m/e 304 [MH]$^+$. A solution of the ketohydrazine (11 g) and triethylamine hydrochloride (2.2 g, 20% w/w) in xylene (500 ml) was heated at reflux for 3 h. The mixture was cooled to room temperature and the solvent evaporated in vacuo. The residue was dissolved in dichloromethane, washed with water (x2), dried (MgSO4) and evaporated in uacuo, and the solid recrystallised (dichloromethanelhexane) to give the title-compound (6.8 g, 58%), $^1$H NMR (360 MHz, CDCl$_3$) δ 2.59 (3H, s, Me), 6.90 (1H, s, Ar—H), 7.95 (1H, m, Ar—H), 8.07 (1H, m, Ar—H), 8.34 (1H, m, Ar—H), 8.78 (1H, s, Ar—H); MS (ES$^+$) m/e 286 [MH]$^+$.

REFERENCE EXAMPLE 1

3-(5-Methylisoxazol-3-yl)-6-(2-pyridyl)methyloxy-1,2,4-triazolo[3,4-a]phthalazine Sodium hydride (244 mg of a 60% dispersion in oil, 6.10 mmol) was added to a stirred solution of 2-pyridylcarbinol (470 mg, 4.27 mol) in DMF (60 ml) at room temperature under nitrogen and the mixture stirred for 0.25 h. After this time, Intermediate 1 (1160 mg, 4.07 mmol) was added and the mixture stirred for 2 h. The solvent was removed in uacuo and the residue dissolved in dichloromethane, washed with water (x2), dried (MgSO$_4$) and evaporated in vacuo. Flash chromatography on silica gel eluting with 3% methanol/dichloromethane followed by recrystallisation (dichloromethane/hexane) gave the title-product (640 mg, 44%), mp 234-236° C.; $^1$H NMR (360 MHz, CDCl$_3$) δ 2.59 (3H, d, J=0.8 Hz, Me), 5.77 (2H, s, CH$_2$), 6.82 (1H, d, J=0.8 Hz, Ar—H), 7.30 (1H, m, Ar—H), 7.74-7.85 (3H, m, Ar—H), 7.95 (1H, m, Ar—H), 8.33 (1H, d, J=7.8 Hz, Ar—H), 8.64-8.72 (2H, m, Ar—H); MS (ES$^+$) m/e 359 [MH]$^+$; Anal. Found. C, 62.93; H, 3.56; N, 22.94. C$_{19}$H$_{14}$N$_6$O$_2$ 0.05 (CH$_2$Cl$_2$) requires C, 63.10; H, 3.92; N; 23.17%.

REFERENCE EXAMPLE 2

6-(6-Bromopyridin-2-yl)methyloxy-3-(5-methylisoxazol-3-yl)-1,2, 4-triazolo[3,4-a]phthalazine The title-compound was prepared from Intermediate 1 and 2-bromopyridine-6-methanol (*Tetrahedron Lett.,* 1996, 50, 2537) following the procedure given for Reference Example 1. The product was isolated by addition of water to the reaction mixture and the resulting precipitate was filtered off. Flash chromatography on silica gel, eluting with ethyl acetate, and recrystallisation (ethyl acetate-methanol) gave the title-phthalazine, mp 247.5-249° C.; $^1$H NMR (360 MHz, CDCl$_3$) δ 2.61 (3H, d, J=0.7 Hz, Me), 5.73 (2H, s, CH$_2$), 6.82 (1H, d, J=0.7 Hz, Ar—H), 7.48 (1H, d, J=7.8 Hz, Ar—H), 7.63 (1H, t, J=7.7 Hz, Ar—H), 7.76 (1H, d, J=7.4 Hz, Ar—H); 7.84 (1H, t, J=8.4 Hz, Ar—H), 7.98 (1H, t, J=8.4 Hz, Ar—H), 8.31 (1H, d, J=8.5 Hz, Ar—H), 8.70 (1H, d, Ar—H); MS (ES$^+$) m/e 437 [MH]$^+$; Anal. Found C, 52.27; H, 2.85; N, 19.14. C$_{19}$H$_{13}$N$_6$O$_2$ Br. 0.1 (H$_2$O) requires C, 51.98; H, 3.03; N, 18.60%.

Intermediate 2

6-Hydroxy-3-(5-Methylisoxazol-3-yl)-1,. 2,4-triazolo[3,4-a]phthalazine

A solution of sodium hydroxide (0.67 g, 17 mmol) in water (7.5 ml) was added to a stirred solution of Intermediate 1 (1.0 g, 3.5 mmol) in dioxane (37.5 ml) and the mixture heated at reflux for 4 h. The solvent was evaporated in vacuo and the residue partitioned between water and diethyl ether. The aqueous layer was separated, washed with ether (x1) and then acidified with 2N hydrochloric acid until pH2 was attained. The solid which precipitated out of solution was filtered off and the aqueous filtrate extracted with dichloromethane (x3). The combined extracts were dried (MgSO$_4$) and evaporated in vacuo and combined with the precipitate to give the title-product (0.45 g, 48%), $^1$H NMR (250 MHz, d$^6$-DMSO) δ 2.58 (3H, d, J=0.7 Hz, Me), 7.07 (1H, d, J=0.9 Hz, Ar—H), 7.94 (1H, m, Ar—H), 8.08 (1H, m, Ar—H), 8.24 (1H, d, J=7.4 Hz, Ar—H), 8.54 (1H, d, J=7.4 Hz, Ar—H), 13.32 (1H, br s, NH); MS (ES$^+$) m/e 268 [MH]$^+$.

REFERENCE EXAMPLE 3

3-(5-Methylisoxazol-3-yl)-6-(1H-1,2,3-triazol-5-yl) methyloxy-1,2,4-triazolo[3,4-a]phthalazine a) 5-Formyl-1-[2-(trimethylsilyl)ethoxy]methyl-1,2,3-triazole n-Butyl lithium (6.8 ml of a 1.6M solution in hexanes, 10.9 mmol) was added dropwise over 0.08h to a stirred solution of 1-[2-(trimethylsilyl)ethoxy]methyl-1,2,3-triazole (J. Heterocycl. Chem., 1992, 29, 1203) (2.077g, 10.42 mmol) in THF (30 ml) at −78° C. under nitrogen. The solution was allowed to warm to −60° C. over 0.67 h, then recooled to −78° C. and DMF (0.9 ml, 11.6 mmol) added. The mixture was allowed to warm to room temperature and stirred for 16.5 h. Saturated ammonium chloride solution (50 ml) was added and the reaction mixture extracted with diethyl ether (3×80 ml). The combined ethereal extrants were dried (MgSO$_4$), evaporated in vacuo, and the residue chromatographed on silica gel, eluting with 30% ethyl acetate/hexane, to give the title-triazole (1.713 g, 72%), $^1$H NMR (360 MH$_2$, CDCl$_3$) δ 0.01 (9H, s, Me$_3$Si), 0.92-0.99 (2H, m, CH$_2$), 3.64-3.69 (2H, m, CH$_2$), 6.05 (2H, s, CH$_2$), 8.31 (1H, s, Ar—H), 10.12 (1H, s, CHO).

b) 5-Hydroxymethyl-1-[2-(trimethylsilyl)ethoxy]methyl-1, 2,3-triazole

Sodium borohydride (0.284 g, 7.51 mmol) was added to a stirred solution of the preceding triazole (1.704 g, 7.495 mmol) in methanol (8 ml) at 0° C. under nitrogen. The mixture was stirred at 0° C. for 0.5 h and at room temperature for 0.5 h. Water was added and the mixture partitioned between dichloromethane and saturated brine. The aqueous layer was separated and further extracted with dichloromethane (x2). The combined organic layers were dried ((MgSO$_4$) and evaporated in vacuo and the residue chromatographed on silica gel, eluting with 70% ethyl acetate/hexane, to give the title-product (1.34 g, 78%), $^1$H NMR (360 MHz, CDCl$_3$) δ 0.00 (9H, s, Me$_3$Si), 0.90-0.95 (2H, m, CH$_2$), 3.58-3.63 (2H, m, CH$_2$), 4.84 (2H, s, CH$_2$), 5.80 (2H, s, CH$_2$), 7.68 (1H, s, Ar—H).

c) 3-(5-Methylisoxazol-3-yl)-6-{1-[2-(trimethylsilyl)ethoxy]methyl-1,2,3-triazol-5-yl}methyloxy-1,2,4-triazolo[3, 4-a]phthalazine The title-compound was prepared from Intermediate 1 and the preceding alcohol following the procedure described for Example 10, 360 MHz (360 MHz, CDCl$_3$) δ 0.00 (9H, s, Me$_3$Si), 0.88-0.93 (2H, m, CH$_2$), 2.63 (3H, s, Me), 3.61-3.66 (2H, m, CH$_2$), 5.92 (2H, s, CH$_2$), 5.97 (2H, s, CH$_2$), 6.89 (1H, s, Ar—H), 7.86 (1H, m, Ar—H), 8.02 (1H, t, J=7.7 Hz, Ar—H), 8.18 (1H, s, Ar—H), 8.23 (1H, d, J=8.0 Hz, Ar—H), 8.76 (1H, d, J=8.0 Hz, Ar—H); MS (ES$^+$) m/e 479 [MH]$^+$.

d) 3-(5-Methylisoxazol-3-yl)-6-(1H-1.2, 3-triazol-5-yl)methyloxy-1.2.4-triazolo[3,4-a]phthalazine A mixture of the preceding product, ethanol (10 ml) and 2N HCl (20 ml) was heated at 50° C. for 15.25 h. The solution was basified to pH 12 with saturated sodium carbonate solution and the solvents evaporated it vacuo. The residue was azeotroped with ethanol (x2) and chromatographed on silica gel, eluting with 0-4% methanol/dichloromethane (gradient elution), to give the title-product, $^1$H NMR (400 MHz, CDCl$_3$) δ 2.65 (3H, s, Me), 5.73 (2H, s, CH$_2$), 7.02 (1H, s, Ar—H), 7.87 (1H, t, J=7.8 Hz, Ar—H), 7.99-8.03 (2H, m, 2 of Ar—H), 8.24 (1H, d, J=8.2 Hz, Ar—H) 8.72 (1H, d, J=7.9 Hz, Ar—H); MS (ES$^+$) m/e 349 [MH]$^+$.

REFERENCE EXAMPLE 4
3-(5-Methylisoxazol-3-yl)-6-(1-methyl-1,2,3-triazol-5-yl)methyloxy-1,2,4-triazolo[3.4-a]phthalazine, 3-(5-methylisoxazol-3-yl)-6-(2-methyl-1,2,3-triazol-4-yl)methyloxy-1,2,4-triazolo[3,4-a]phthalazine and 3-(5-methylisoxazol-3-yl)-6-(1-methyl-1,2,3-triazol-4-yl)methyloxy-1,2,4-triazolo[3,4-a]phthalazine Lithium hexamethyldisilazide (1.63 ml of a IM solution in THF, 1.63 mmol) was added dropwise to a stirred solution of 3-(5-methylisoxazol-3-yl)-6-(1H-1,2,3-triazol-5-yl)methyloxy-1,2,4-triazolo[3,4-a]phthalazine (241 mg, 0.626 mmol) prepared as in Reference Example 3 in DMF (50 ml) at −31° C. under nitrogen. The mixture was warmed to −23° C. over 1.5 h, methyl iodide (0.10 ml, 1.6 mmol) added dropwise and the reaction mixture allowed to warm to room temperature overnight. Water was added and the solvent evaporated in vacuo. The residue was partitioned between dichloromethane and water and the aqueous phase separated and re-extracted with dichloromethane (x1). The combined organic extrants were washed with brine (x1), dried (MgSO$_4$) and evaporated in vacuo. Chromatography of the residue on silica gel, eluting with 0-5% methanol/dichloromethane (gradient elution), followed by preparative HPLC (YMC Sil column, 250×20 mm) eluting with 5% methanol/1-chlorobutane, separated the triazole isomers:
Least polar isomer (HPLC solvent system): 3-(5-methylisoxazol-3-yl)-6-(2-methyl-1,2,3-triazol-4-yl)methyloxy-1,2,4-triazolo[3,4-a]phthalazine $^1$H NMR (400 MHz, CDCl$_3$) δ 2.59 (3H, s, Me), 4.21 (3H, s, Me), 5.73 (2H, s, CH$_2$), 6.89 (1H, s, Ar—H), 7.79 (1H, m, Ar—H), 7.94 (1H, m, Ar—H), 8.10 (1H, s, Ar—H), 8.22 (1H, d, J=8.0 Hz, Ar—H), 8.67 (1H, d, J=8.0 Hz, Ar—H); MS (ES$^+$) m/e 363 [MH]$^+$.

Intermediate polarity isomer: 3-(5-methylisoxazol-3-yl)-6-(1-methyl-1,2,3-triazol-4-yl)methyloxy-1,2,4-triazolo[3, 4-a]phthalazine $^1$H NMR (400 MHz, CDCl$_3$) δ 2.60 (3H, s, Me), 4.09 (3H, s, Me), 5.78 (2H, s, CH$_2$), 6.90 (1H, d, J=0.8 Hz, Ar—H), 7.80 (1H, m, Ar—H), 7.94 (1H, m, Ar—H), 8.25 (1H, d, J=8.0 Hz, Ar—H), 8.65 (1H, d, J=8.0 Hz, Ar—H), 8.73 (1H, s, Ar—H); MS (ES$^+$) m/e 363 [MH]$^+$.

Most polar isomer (HPLC solvent system): 3-(5-methylisoxazol-3-yl)-6-(1-methyl-1,2,3-triazol-5-yl)methyloxy-1,2,4-triazolo[3,4-a]phthalazine $^1$H NMR (400 MHz, CDCl$_3$) δ 2.56 (3H, s, Me), 4.19 (3H, s, Me), 5.76 (2H, s, CH$_2$), 6.82 (1H, s, Ar—H), 7.80 (1H, m, Ar—H), 7.96 (1H, m, Ar—H), 8.04 (1H, s, Ar—H), 8.12 (1H, d, J=8.8 Hz, Ar—H), 8.67 (1H, d, J=8.0 Hz, Ar—H); MS (ES$^+$) m/e 363 [MH]$^+$.

EXAMPLE 1

Figure 8:
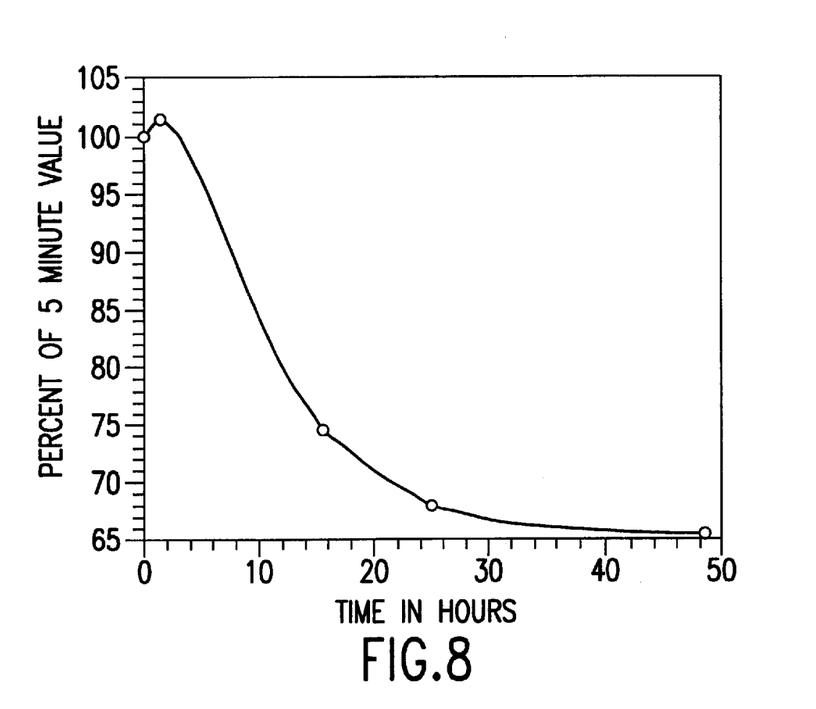
FIG. 8 shows the time-dependent concentration of 3-(5-methylisoxazol-3-yl)-6-(1-methyl-1,2,3-triazol-4-yl)methyloxy-1,2,4-triazolo [3,4-a]phthalazine in 2.5% pamoate solution.

Time Dependence of 3-(5-methylisoxazol-3-yl)-6-(1-methyl-1,2,3-triazol-4-yl)methyloxy-1,2,4-triazolo[3,4-a]phthalazine Solubility To a stirred, light protected glass vial was added 23.0 mL 2.5% aqueous di-sodium pamoate solution and 42 mg 3-(5-methylisoxazol-3-yl)-6-(1-methyl-1,2,3-triazol-4-yl)methyloxy-1,2,4-triazolo[3,4-a]phthalazine. Aliquots were removed by 3 mL syringe at various time intervals, passed through 0.22 μm Millex-GV low protein binding syringe filters, and diluted to appropriate concentrations with 50/50 MeCN/H$_2$O for HPLC analysis. HPLC quantitation against appropriate standards showed a significant decrease in solubility over time approaching 65% of the original solubility after 5 minutes (Table 1). These data are plotted on FIG. 8.

TABLE 1

L-822, 179 Time Dependent Solubility by HPLC in mg/mL

| Minutes | Hours | Concentration | % of 5 Minute Value |
|---|---|---|---|
| 5 | 0.08 | 1.89 | 100.0 |
| 90 | 1.50 | 1.92 | 101.4 |
| 930 | 15.5 | 1.41 | 74.5 |
| 1500 | 25.0 | 1.29 | 68.0 |
| 2910 | 48.5 | 1.24 | 65.4 |

The time dependence of the solubility is consistent with slow conversion of the original anhydrous crystal form to another of greater stability and less solubility in this medium. Subsequent experiments tracking this time dependence under a variety of conditions (container changes, light protection, nitrogen purge, pamoate concentration) support this hypothesis rather than adsorption or additional chemical reactions. Also, the anhydrous form is already highly crystalline by XRPD analysis, suggesting that a crystallization of an amorphous form is not responsible.

EXAMPLE 2

Synthesis of Di-hydrate in 5% Di-sodium Pamoate Solution

To an Eppendorf tube was added 1 mL 5% aqueous di-sodium pamoate solution and 25 mg 3-(5-methylisoxazol-3-yl)-6-(1-methyl-1,2,3-triazol-4-yl)methyloxy-1,2,4-triazolo[3,4-a]phthalazine . The resulting suspension was vortexed for 1 minute, placed on a rotary mixer for 10 minutes, then centrifuged at 13,000 rpm for 5 minutes, forcing non-dissolved starting material to the bottom. Three dops of supernatant were removed for tonicity measurements (238, 241, 237 mmol/kg). The tube was then resealed, light protected with aluminium foil, vortexed for 1 minute and replaced on the rotary mixer for 48 hours. The solids were then vacuum filtered off and rinsed with 2×1 mL water, followed by washing and tituration with 2 mL more. Solids were partially wet when first analyzed by XRPD, afterward they were dried by house vacuum for 48 hours before more XRPD analysis.

Partial Synthesis of Di-hydrate in Water

To an Eppendorf tube was added 1 mL USP water and 20 mg 3-(5-methylisoxazol-3-yl)-6-(1-methyl-1,2, 3-triazol-4-yl)methyloxy-1,2, 4-triazolo[3,4-a]phthalazine. The resulting suspension was vortexed for 10 seconds, then light protected with aluminium foil and placed on a rotary mixer for 72 hours. The solids were then vacuum filtered off and rinsed with 2xl mL water. Solids were partially wet when first analyzed by XRPD, afterward they were dried by house vacuum for 48 hours before more XRPD analysis.

Analysis

The XRPD data have been described earlier with the exception of the incompletely converted material from the synthesis in water. FIG. 10 shows the XRPD pattern of the anhydrous form (bottom), di-hydrate synthesised from di-sodium pamoate solution (top), and the mixture of anhydrous and hydrated forms resulting from 72 hours exposure of the anhydrous form to pure water. This data suggests that the conversion to the hydrated form is kinetically limited by the extreme insolubility of the anhydrous form in pure water. Conversion may take place more rapidly if solubility is increased by the addition of di-sodium pamoate or by other means. The di-hydrate may also be prepared using a 10% solution of MeCN in water.

EXAMPLE 3

Synthesis of 3-(5-methylisoxazol-3-yl)-6-(1-methyl-1,2,3-triazol-4-yl)methyloxy-1,2,4-triazolo[3,4-a]phthalazine Dehydrate To an Eppendorf tube was added 1.5 mL 5% aqueous di-sodium pamoate solution and 100 mg 3-(5-methylisoxazol-3-yl)-6-(1-methyl-1,2,3-triazol-4-yl) methyloxy-1,2,4-triazolo[3,4-a]phthalazine. The resulting suspension was vortexed for 10 seconds, light protected with aluminium foil and placed on a rotary mixer for 4 days. Crystals were removed by vacuum filtration, rinsing and titurating with 10 mL water. Crystals were placed in a vial under house vacuum overnight, then were identified by XRPD as the di-hydrate. Half of these crystals were then sonicated in 3 mL water for 7 minutes, wrapped in foil and placed on the rotary mixer overnight. Following another brief sonication, these crystals were vacuum filtered, rinsed with 15 mL water, dried in a vacuum oven at 45° C. for 20.5 hours, removed and analysed by XRPD, TGA and DSC as described earlier.

EXAMPLE 4

Preparation of 3-(5-methylisoxazol-3-yl)-6-(1-methyl-1,2,3-triazol-4-yl)methyloxy-1,2,4-triazolo[3,4-a]phthalazine Dihydrate Crude 3-(5-methylisoxazol-3-yl)-6-(1-methyl-1,2,3-triazol-4-yl)methyloxy-1,2,4-triazolo[3,4-a]phthalazine (30 g, 0.08 mol) was dissolved in glacial acetic acid (390 ml) and water (90 ml) at 77° C. The solution was filtered hot through a medium sintered glass funnel. To the solution at 45° C. was added water (1860 ml) over 10 min. The mixture was aged at ambient temperature for 17 h, filtered and washed with water (2×300 ml). The product was air dried to constant weight to yield 32 g of the dihydrate.

EXAMPLE 5

Formulation of enterically coated tablets of 3-(5-methylisoxazol-3-yl)-6-(1-methyl-1,2,3-triazol-4-yl) methyloxy-1,2,4-triazolo[3,4-a]phthalazine with disodium pamoate 3-(5-Methylisoxazol-3-yl)-6-(1-methyl-1,2,3-triazol-4-yl)methyloxy-1,2,4-triazolo[3,4-a]phthalazine dihydrate (0.99 g) was dry mixed by glass mortar and pestle with disodium pamoate (3.6 g), HPC-LF (0.225 g) and Avicel PH-102 (1.155 g) until a uniform mixture was apparent. Small amounts of water (1.75 g total) were added and mixed into the powder until granules were obtained. The granules were sieved through a #35 mesh screen and permitted to air dry for 7 days. Dried granules (2.43 g) were jar mixed with PVPP (0.0972 g) for 2 minutes. Ten tablets (nominal weight 208 mg) were compressed from the granulate on a Carver press using 11/32 RSC tooling at 0.8 tons of force. The tablets were introduced to 900 g of placebo tablets and warmed to 40° C. in the Freund HCT30 #260, after which a 15% w/w SURERELEASE dispersion in water was applied until a 10% weight gain was achieved. The resulting enteric coated tablets were stored at RT for future use.

What is claimed is:

1. A composition comprising pamoate ions and an active compound wherein said active compound comprises a species neutral at pH 6 or less.

2. A composition according to claim 1 comprising a solution.

3. A composition according to claim 1 which is solid and further comprises a cation.

4. A composition according to claim 1 comprising a pharmaceutical or veterinary composition. or veterinary composition.

5. A pharmaceutical or veterinary composition comprising a pharmaceutical or veterinary compound neutral at pH 6 or less, pamoate ions, optionally a pharmaceutically or veterinally acceptable cation, and an enteric coating.

6. A composition according to claim 1 wherein the neutral species is 3-(5-methylisoxazol-3-yl)-6-(1-methyl-1,2,3-triazol-4-yl)methyloxy-1,2,4-triazolo[3,4-a]phthalazine.

7. A composition according to claim 5 wherein the neutral pharmaceutical or veterinary compound comprises 3-(5-methylisoxazol-3-yl-6-(1-methyl-1,2,3- triazol-4-yl) methyloxy-1,2,4-triazolo[3,4-a]phthalazine.

8. A method of solubilizing molecules that are neutral at pH 6 or less, said method comprising the step of admixing pamoate ions with said neutral molecules.

* * * * *